United States Patent [19]

Nakagawa

[11] Patent Number: 4,814,520
[45] Date of Patent: Mar. 21, 1989

[54] PROCESS FOR PRODUCING 2,2-BIS(4'HYDROXYPHENYL) PROPANES

[75] Inventor: Takashi Nakagawa, Tokuyama, Japan

[73] Assignee: Idemitsu Petrochemical Company Limited, Tokyo, Japan

[21] Appl. No.: 91,794

[22] Filed: Sep. 1, 1987

[30] Foreign Application Priority Data

Sep. 2, 1986 [JP] Japan .................................. 61-207459

[51] Int. Cl.$^4$ .................................................. C07C 39/16
[52] U.S. Cl. ........................................ 568/723; 568/722
[58] Field of Search .................................. 568/722, 723

[56] References Cited

U.S. PATENT DOCUMENTS 2,884,462   4/1959   Henry ............................ 568/722
4,239,918  12/1980   Keeley ........................... 568/722

FOREIGN PATENT DOCUMENTS 687800    6/1964   Canada ............................... 568/723
912288   12/1962   United Kingdom ............... 568/722
1187684   4/1970   United Kingdom ............... 568/723

Primary Examiner—Werren B. Lone
Attorney, Agent, or Firm—Armstrong, Nikaido, Marmelstein & Kubovcik

[57] ABSTRACT

Disclosed is a process for producing 2,2-bis(4'-hydroxyphenyl)propanes represented by the following general formula (2):

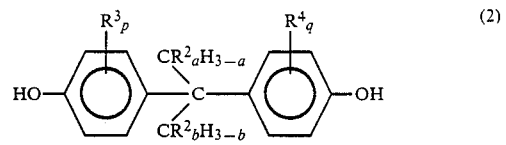

(wherein $R^2$ represents hydrogen atom or a hologen atom and the four $R^2$ may be identical or different, $R^3$ and $R^4$ which may be identical or different represent hydrogen atom, an alkyl group, an aryl group, an aralkyl group, a cycloalkyl group, an alkoxy group or a halogen atom, p and q which may be identical or different represent integers of 1-4, a is 2 or 3 and b is 2 when a is 2 and is 1 when a is 3), characterized by reacting at least one phenol represented by the following formula (1):

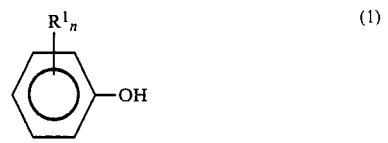

(wherein $R^1$ has the same meaning as $R^3$ and $R^4$ and n is an integer of 1-4) with an unsaturated carbon compound represented by the general formula: $C_3R_4^2$ (wherein $R^2$ has the same meaning as in the formula (2) and the four $R^2$ may be identical or different) in the presence of hydrochloric acid.

9 Claims, 1 Drawing Sheet

PROCESS FOR PRODUCING 2,2-BIS(4'HYDROXYPHENYL) PROPANES

BACKGROUND OF THE INVENTION

This invention relates to a process for production of 2,2-bis(4'-hydroxyphenyl)propanes used as starting materials for production of polycarbonate resins and epoxy resins and more particularly it relates to a process for production of 2,2-bis(4'-hydroxyphenyl)propanes by reacting a phenol compound with, for example, an unsaturated carbon compound in the presence of hydrochloric acid.

For production of 2,2-bis(4'-hydroxyphenyl)propanes (sometimes referred to as "bisphenol A" hereinafter), there have been known a process comprising condensing a phenol with acetone in the presence of an ion exchange resin (cf. Japanese patent examined publication No. 981/62), a process comprising reacting a phenol with an aliphatic unsaturated hydrocarbon represented by the general formula $C_3H_4$ in the presence of, for example, Lewis acid such as boron trifluoride or aluminum trichloride or sulfuric acid (U.S. Pat. No. 2,884,462), etc.

However, the process using ion exchange resin has the problems that since water which is a reaction by-product reduces the activity of the ion exchange resin, yield of bisphenol A gradually decreases when reaction is carried out continuously for a long period of time. On the other hand, the process using Lewis acid or sulfuric acid as a catalyst (U.S. Pat. No. 2,884,462) has also problems, in addition to low selectivity of bisphenol (68%), that the treatment is complicated because the Lewis acid as catalyst must be deactivated and removed by neutralization of the Lewis acid in order to obtain bisphenols of high purity. Furthermore, in this process the deactivated and removed Lewis acid cannot be repeatedly used as catalyst and hence cost of catalyst is high.

SUMMARY OF THE INVENTION

The object of this invention is to provide a process for production of bisphenols which is free from the problems such as reduction of yield of bisphenols with formation of by-products and low purity of the bisphenols obtained as seen in the process using ion exchange resin and furthermore the problems such as low selectivity of the bisphenols, complicated operation for obtaining high purity bisphenols and high cost of catalyst as seen in the process using Lewis acid and according to which selectivity of bisphenols is high, high purity bisphenols can be obtained by simple operation and besides cost of catalyst is low.

As a result of the inventors' intensive researches, it has been found that above object can be accomplished by using hydrochloric acid as a catalyst in the reaction of a phenol compound and an unsatuated aliphatic hydrocarbon represented by the general formula $C_3R_4$ and this invention has been attained.

That is, this invention for accomplishing the above object is a process for producing 2,2-bis(4'-hydroxyphenyl)propanes (sometimes referred to as "bisphenols" hereinafter) represented by the following general formula (2):

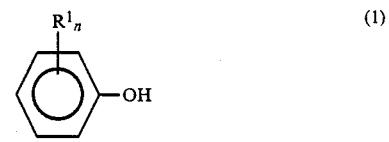

(wherein $R^2$ represents hydrogen atom or a halogen atom and the four $R^2$ may be identical or different, $R^3$ and $R^4$ which may be identical or different represent hydrogen atom, an alkyl group, an aryl group, an aralkyl group, a cycloalkyl group, an alkoxy group or a halogen atom, p and q which may be identical or different represent integers of 1–4, a is 2 or 3 and b is 2 when a is 2 and is 1 when a is 3), characterized by reacting at least one phenol represented by the following formula (1):

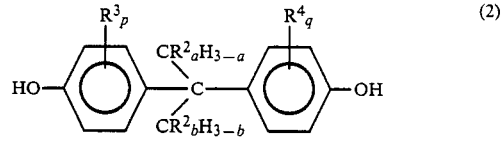

(wherein $R^1$ has the same meaning as $R^3$ and $R^4$ and n is an integer of 1–4) with an unsaturatead carbon compound represented by the general formula: $C_3R_4^2$ (wherein $R^2$ has the same meaning as in the formula (2) and the four $R^2$ may be identical or different) in the presence of hydrochloric acid.

DESCRIPTION OF THE INVENTION

Figure 1:
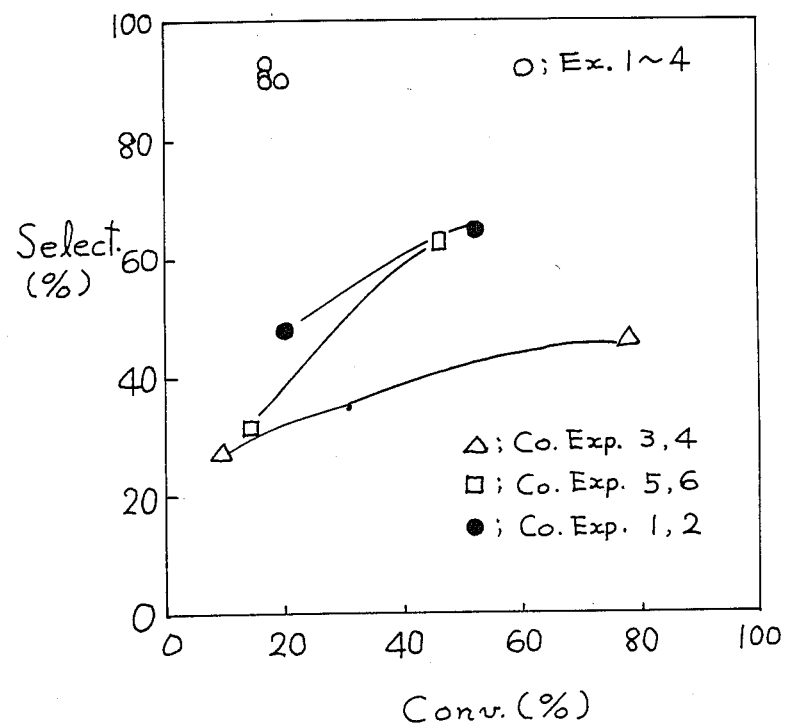
FIG. 1 is a graph which shows relation between the conversion rate and selectivity of bisphenols in Examples 1–4 and Comparative Examples 1–6.

It is preferred to use sufficiently purified phenols, but those containing water may also be used as far as they do not prevent accomplishment of the object of this invention.

The phenols can be represented by the following formula (1):

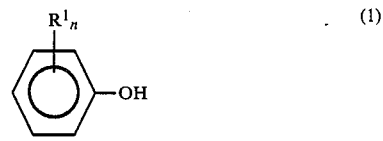

(wherein $R^1$ represents hydrogen atom, an alkyl group, an aryl group, an aralkyl group, cycloalkyl group, an alkoxy group or a halogen atom and n is an integer of 1–4).

As examples of the phenols, mention may be made of phenol, 2-methyphenol, 3-methylphenol, 4-methylphenol, ethylphenol, propylphenol, 2-t-butylphenol, 2-t-amylphenol,, 2-sec-amylphenol, 4-octylphenol, 4-nonylphenol, 2,6-dimethylphenol 2,6-diethylphenol, 2,6-diisopropylphenol, 2,6-di-t-butylphenol, di-t-amylphenol, di-sec-amylphenol, 2-phenylphenol, 2,6-diphenylphenol, 2,3-diphenylphenol, 2-benzylphenol, 2,6-dibenzylphenol, 2-methoxyphenol, 3-methoxyphenol, 4-methoxyphenol, 2-ethoxyphenol, 3-ethoxyphenol, 4-ethoxyphenol, 2,6-diethoxyphenol 2,6-diethoxyphenol, 2-cyclohexylphenol, 2,6-dicyclohexylphenol, 2,3-dicyclohexylphenol, 2-chlorophenol, 2-fluorophenol, 2-bromophenol, 2,6-dichlorophenol, 2,6-difluorophenol, 2,6-dibromophenol, etc.

This invention is not limited to use of these exemplified phenols and there are no limitations in the number of substituent $R^1$ and position of substitution. When 2,2-bis(4'-hydroxyphenyl)propanes of preferable properties should be produced, it is desirable to use phenols of good symmetricalness. This is because use of phenols of good symmetricalness as a starting material can afford 2,2-bis(4'-hydroxyphenyl)propanes of good symmetricalness and 2,2-bis(4'-hydroxyphenyl)propanes of good symmetricalness can afford polycarbonates superior in mechanical properties such as heat resistance and stiffness.

Therefore, phenols preferred in this invention can be represented by the following formula (3):

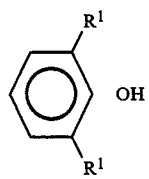
(3)

(wherein $R^1$ has the same meaning as above).

Especially preferred among those represented by the formula (3) are as follows: 2-methylphenol, 2,6-dimethylphenol, 2-isopropylphenol, 2-methoxyphenol, 2,6-dimethoxyphenol, 2-cyclohexylphenol, 2,6-dicyclohexylphenol, 2-chlorophenol, 2,6-dichlorophenol, 2-fluorophenol, 2,6-difluorophenol, 2-bromophenol, 2,6-dibromophenol, etc.

These phenols may be used alone or in combination of two or more. When 2,2-bis(4'-hydroxyphenyl)propanes of good symmetricalness are to be produced, it is preferred to use one phenol alone.

The unsaturated aliphatic carbon compounds represented by the general formula $C_3R_4^2$ include methylacetylenes represented by the following formula (4):

(wherein $R^2$ represents hydrogen atom or halogen atom and the four $R^2$ may be identical or different) and propadienes represented by the following formula (5):

(wherein $R^2$ has the same meaning as above).

Preferable unsaturated aliphatic carbon compounds represented by the general formula $C_3R_4^2$ are methylacetylenes represented by the formula (4) and more preferred are methylacetylene and trifluoromethylfluoroacetylene ($CF_3C \equiv CF$).

In this invention, either of said methylacetylenes or propadienes may be used alone or they may be used in admixture.

Hydrochloric acid used in this invention is used as an aqueous hydrochloric acid solution of usually 5–100% by weight, preferably 20–36% by weight in hydrogen chloride concentration. When concentration of hydrogen chloride is less than 5% by weight, action as a catalyst sometimes cannot be fully exhibited.

In this invention, said phenols and said unsaturated aliphatic carbon compounds represented by the general formula $C_3R_4^2$ are reacted in the presence of said hydrochloric acid. This reaction can be expressed by the following equation (6):

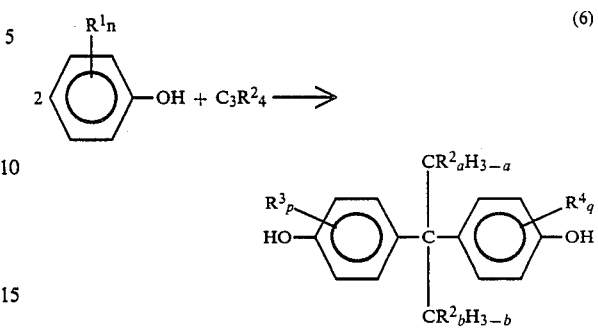

(wherein $R^1$, $R^2$, $R^3$, $R^4$, a and b have the same meanings as above).

Among those bisphenols obtained by the process of this invention, preferred are those of good symmetricalness in molecular structure.

As bisphenols of good symmetricalness, mention may be made of, for example,
2,2-bis(4'-hydroxyphenyl)propane,
2,2-bis(3'-methyl-4'-hydroxyphenyl)propane,
2,2-bis(3',5-dimethyl-4'-hydroxyphenyl)propane,
2,2-bis(3'-isopropyl-4'-hydroxyphenyl)propane,
2,2-bis(3',5-diisopropyl-4'-hydroxyphenyl)propane,
2,2-bis(3'-methoxy-4'-hydroxyphenyl)propane,
2,2-bis(3',5-dimethoxy-4'-hydroxyphenyl)propane,
2,2-bis(3'-cyclohexyl-4'-hydroxyphenyl)propane,
2,2-bis(3',5-dicyclohexyl-4'-hydroxyphenyl)propane,
2,2-bis(3'-chloro-4'-hydroxyphenyl)propane,
2,2-bis(3',5-dichloro-4'-hydroxyphenyl)propane,
2,2-bis(3'-fluoro-4'-hydroxyphenyl)propane,
2,2-bis(3',5-difluoro-4'-hydroxyphenyl)propane,
2,2-bis(3'-bromo-4'-hydroxyphenyl)propane,
2,2-bis(3',5-dibromo-4'-hydroxyphenyl)propane,
2,2-bis(4'-hydroxyphenyl)hexahalopropane,
2,2-bis(3'-methyl-4'-hydroxyphenyl)tetrahalopropane,
2,2-bis(3',5-dimethyl-4'-hydroxyphenyl)tetrahalopropane,
2,2-bis(3'-isopropyl-4'-hydroxyphenyl)tetrahalopropane,
2,2-bis(3',5-diisopropyl-4'-hydroxyphenyl)tetrahalopropane,
2,2-bis(3'-methoxy-4'-hydroxyphenyl)tetrahalopropane,
2,2-bis(3',5-dimethoxy-4'-hydroxyphenyl)tetrahalopropane,
2,2-bis(3'-cyclohexyl-4'-hydroxyphenyl)tetrahalopropane,
2,2-bis(3',5-dicyclohexyl-4'-hydroxyphenyl)tetrahalopropane,
2,2-bis(3'-chloro-4'-hydroxyphenyl)tetrahalopropane,
2,2-bis(3',5-dichloro-4'-hydroxyphenyl)tetrahalopropane,
2,2-bis(3'-fluoro-4'-hydroxyphenyl)tetrahalopropane,
2,2-bis(3',5-difluoro-4'-hydroxyphenyl)tetrahalopropane,
2,2-bis(3'-bromo-4'-hydroxyphenyl)tetrahalopropane,
2,2-bis(3',5-dibromo-4'-hydroxyphenyl)tetrahalopropane, etc.

Reaction temperature in this reaction is usually 30°–180° C., preferably 40°–100° C. When the reaction temperature is lower than 30° C., the layer containing phenols is apt to harden and when higher than 180° C., the reaction is a vapor phase reaction and so control of the reaction system becomes difficult.

Reaction pressure is usually 0–10 kg/cm$^2$, preferably 1–5 kg/cm$^2$. The reaction may also be effected under reduced pressure. When the reaction pressure is higher than 10 kg/cm$^2$, there is the tendency of increase in possibility of explosion of the unsaturated carbon compounds such as methylacetylenes.

Reaction time is normally 1 hour or more, preferably 3 hours or more. When it is less than 1 hour, conversion rate of phenols decreases with decrease in selectivity of bisphenols.

Amount of hydrochloric acid is adjusted so that the weight ratio hydrochloric acid/phenols is 0.1 or more, preferably 0.5–2. When the weight ratio is less than 0.1, conversion rate of phenols decreases with reduction of selectivity of bisphenols.

In this invention, the reaction mixture is allowed to stand to cause separation into a layer containing phenol and a hydrochloric acid layer and hence operation for removal of hydrochloric acid is not needed. The reaction product bisphenol can be obtained from the upper phenol-containing layer by crystallization. The hydrochloric acid can be repeatedly used.

The bisphenols obtained by the process of this invention are us useful, for example, as starting materials for polycarbonate resins.

The process for production of 2,2-bis(4'-hydroxyphenyl)propanes according to this invention has the following advantages.

(1) According to the process of this invention, high purity 2,2-bis(4'-hydroxyphenyl)propanes can be produced stably for a long period of time.

(2) According to the process, since the phenols and hydrochloric acid in the reaction mixture separate into two layers only by allowing the reaction mixture to stand still, there is no need to neutralize catalyst and remove the deactivated catalyst as in the conventional process using a Lewis acid as a catalyst and besides, 2,2-bis(4'-hydroxyphenyl)propanes can be obtained from the phenol-containing layer by crystallization. Furthermore, hydrochloric acid separated from the phenol-containing layer is not deactivated and so can be repeatedly used. Therefore, this invention can provide a simple and economical process for producing 2,2-bis(4'-hydroxyphenyl)propanes.

(3) According to the process of this invention, 2,2-bis(4'-hydroxyphenyl)propanes can be produced at higher selectivity than in the conventional processes.

Example 1

30 g of phenol was charged in a 200 ml four-necked flask and the atmosphere in the flask was replaced with methylacetylene, followed by adding 30 g of 30 wt% hydrochloric acid with stirring to carry out the reaction at reaction temperature of 90° C. for a reaction time of 5 hours. Then, the reaction mixture was left to stand still and the phenol layer (upper layer) was taken and subjected to gas chromatography assay. Reaction conditions and the results are shown in Table 1.

Example 2

Example 1 was repeated except that 36 wt% hydrochloric acid was used and a reaction temperature of 75° C. was employed. Reaction conditions and the results are shown in Table 1.

Example 3

Example 2 was repeated except that a reaction temperature of 83° C. was employed. Reaction conditions and the results are shown in Table 1.

Example 4

Example 2 was repeated except that a reaction temperature of 90° C. was employed. Reaction conditions and the results are shown in Table 1.

Example 5

Reaction was effected under the same conditions as in Example 1 and thereafter, the reaction mixture was separated into phenol layer and hydrochloric acid layer. This phenol solution was subjected to crystallization at 50° C. and the crystal was collected by filtration to obtain a 1:1 complex. Thus obtained complex crystal was subjected to distillation under reduced pressure (160° C., 5 mmHg) to remove phenol therefrom to obtain bisphenol. To the filtrate after removal of the complex crystal were added phenol in an amount corresponding to that consumed in the reaction and hydrochloric acid separated hereabove and thereafter, the reaction under the same conditions as in example 1 was repeated.

In order to show the superiority of this invention, relation between conversion rate and selectivity of bisphenol in Examples 1–4 and Comparative Examples 1–6 is shown in FIG. 1.

Sulfuric acid catalyst and hydrochloric acid catalyst which afforded nearly the same conversion rate are considered to have nearly the same catalyst activity.

As is evident from FIG. 1, when selectivities in Examples of this invention and in Comparative Examples are compared, for example, at a conversion rate of 30%, those in Examples are markedly higher than those in Comparative Examples.

Therefore, the process of this invention is superior in selectivity to the conventional processes.

TABLE 1

| | | Unit | Examples | | | | | |
| --- | --- | --- | --- | --- | --- | --- | --- | --- |
| | | | 1 | 2 | 3 | 4 | 6 | 7 |
| Catalyst | Compound | — | Hydrochloric acid | Hydrochloric acid | Hydrochloric acid | Hydrochloric acid | Hydrochloric acid | Hydrochloric acid |
| | Concentration | wt % | 30 | 36 | 36 | 36 | 30 | 30 |
| | Catalyst/Phenol | wt ratio | 1 | 1 | 1 | 1 | 1 | 1 |
| Reaction temperature | | °C. | 90 | 75 | 83 | 90 | 90 | 90 |
| Reaction pressure | | kg/cm$^2$ | 1 | 1 | 1 | 1 | 1.5 | 2.0 |
| Reaction time | | hr | 5 | 5 | 5 | 5 | 3 | 3 |
| Conversion rate of phenol | | mol % | 20 | 17 | 17 | 17 | 22 | 40 |
| Selectivity of bisphenol | | mol % | 90 | 93 | 90 | 91 | 91 | 90 |
| | | Unit | Comparative Examples | | | | | |
| | | | 1 | 2 | 3 | 4 | 5 | 6 |
| Catalyst | Compound | — | Ion ex- | Ion ex- | Sulfuric acid | Sulfuric acid | Boron | Boron |

TABLE 1-continued

|  |  | change resin | change resin |  |  | trifluoride | trifluoride |
|---|---|---|---|---|---|---|---|
| Concentration | wt % | 4.7 | 4.7 | 97 | 97 | — | — |
| Catalyst/Phenol | wt ratio | 0.3 | 0.3 | 0.3 | 0.02 | 0.03 | 0.003 |
| Reaction temperature | °C. | 55 | 55 | 55 | 55 | 55 | 55 |
| Reaction pressure | kg/cm² | 1 | 1 | 1 | 1 | 1 | 1 |
| Reaction time | hr | 5 | 1 | 5 | 5 | 5 | 5 |
| Conversion rate of phenol | mol % | 52 | 20 | 78 | 9 | 46 | 14 |
| Selectivity of bisphenol | mol % | 65 | 48 | 46 | 27 | 63 | 31 |

: milli equivalent/g

TABLE 2

| Recycling number | | Reaction | | | Crystallization | | |
|---|---|---|---|---|---|---|---|
| | | Concentration of bisphenol (wt %) | Convession rate of phenol (%) | Selectivity of bisphenol (%) | Concentration of bisphenol in filtrate (wt %) | Concentration of bisphenol in crystal (wt %) | Crystallization temperature (°C.) |
| 1 | A | 17 | 15 | 90 | 20 | 34 | 50 |
|   | B | 32 |    |    |    |    |    |
| 2 | A | 18 | 18 | 90 | 19 | 33 | 50 |
|   | B | 36 |    |    |    |    |    |
| 3 | A | 17 | 17 | 90 | 21 | 33 | 50 |
|   | B | 34 |    |    |    |    |    |
| 4 | A | 18 | 18 | 90 | 21 | 32 | 50 |
|   | B | 36 |    |    |    |    |    |
| 5 | A | 17 | 17 | 90 | 22 | 33 | 50 |
|   | B | 34 |    |    |    |    |    |

A: Before reaction
B: After reaction

What is claimed is:

1. A process for producing 2,2-bis(4'-hydroxyphenyl)propane represented by the following formula (2):

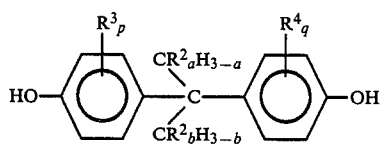

(2)

wherein $R^2$ represents a hydrogen atom or a halogen atom and each $R^2$ may be identical or different; $R^3$ and $R^4$ which, may be identical or different, each represents a hydrogen atom, an alkyl group, an aryl group, an aralkyl group, a cycloalkyl group, an alkoxy group or a halogen atom; p and q, which may be identical or different, each represents an integer of 1-4; a is 2 or 3; and b is 2 when a is 2 and 1 when a is 3, which comprises reacting at least one phenol represented by the following formula (1):

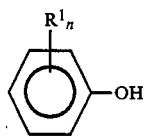

(1)

wherein $R^1$ has the same meaning as $R^3$ and $R^4$ and n is an integer of 1-4, with an unsaturated carbon compound represented by the formula $C_3R^2_4$, wherein $R^2$ has the same meaning as above and the four $R^2$ may be identical or different, in the presence of hydrochloric acid at a temperature of 30°-180° C. and pressure of 0-10 kg/cm².

2. A process according to claim 1 wherein $R^2$, $R^3$ and $R^4$ are at least one group selected from the group consisting of lower alkyl group of 1-5 carbon atoms, phenyl group which may be substitited with lower alkyl group of 1-5 carbon atoms, halogen atom and hydrogen atom and $R^2$ is at least one atom selected from the group consisting of hydrogen atom and fluorine atom.

3. A process according to claim 1 wherein $R^1$, $R^3$ and $R^4$ are at least one group or atom selected from the group consisting of methyl group, hydrogen atom and bromine atom and $R^2$ is hydrogen atom.

4. A process according to claim 1 wherein $R^1$, $R^2$, $R^3$ and $R^4$ are hydrogen atoms.

5. A process according to claim 1 wherein the unsaturated carbon compound is an unsaturated hydrocarbon.

6. A process according to claim 1 wherein the unsaturated carbon compound is methylacetylene.

7. A process according to claim 1 wherein hydrochloric acid is used as an aqueous hydrochloric acid solution having a hydrogen chloride concentration of 5-100% by weight.

8. A process according to claim 1 wherein hydrochloric acid is used as an aqueous hydrochloric acid solution having a hydrogen chloride concentration of 20-36% by weight.

9. A process according to claim 2 wherein $R^1$, $R^2$, $R^3$ and $R^4$ are hydrogen atoms.

* * * * *